(12) United States Patent  (10) Patent No.: US 9,238,137 B2
Einav et al.  (45) Date of Patent: Jan. 19, 2016

(54) NEUROMUSCULAR STIMULATION (75) Inventors: Omer Einav, Emek Hefer (IL); Ernesto Korenman, RaAnana (IL)

(73) Assignee: Motorika Limited, Hamilton (BM)

( * ) Notice: Subject to any disclaimer, the term of this patent is extended or adjusted under 35 U.S.C. 154(b) by 1570 days.

(21) Appl. No.: 10/597,602

(22) PCT Filed: Feb. 4, 2005

(86) PCT No.: PCT/IL2005/000135
§ 371 (c)(1),
(2), (4) Date: May 8, 2008

(87) PCT Pub. No.: WO2005/087307
PCT Pub. Date: Sep. 22, 2005

(65) Prior Publication Data
US 2008/0234781 A1  Sep. 25, 2008

Related U.S. Application Data

(60) Provisional application No. 60/542,022, filed on Feb. 5, 2004, provisional application No. 60/566,078, filed on Apr. 29, 2004.

(51) Int. Cl.
*A61N 1/18* (2006.01)
*A61N 1/36* (2006.01)

(52) U.S. Cl.
CPC ........ *A61N 1/36003* (2013.01); *A61N 1/36014* (2013.01)

(58) Field of Classification Search
CPC ... A61N 1/0456; A61N 1/0476; A61N 1/205; A61N 1/3702; A61N 1/36003; A61N 1/36014; A61B 5/04001; A61B 5/04004; A61B 5/04008; A61B 5/053; A61B 5/11; A61B 5/1101; A61B 5/1107; A61B 5/1121; A61B 5/45; A61B 5/6824; A61B 5/6828
USPC ................................ 607/2, 48, 115
See application file for complete search history.

(56) References Cited

U.S. PATENT DOCUMENTS 3,745,990 A  7/1973 Neis
3,824,991 A  7/1974 Whitaker
(Continued)

FOREIGN PATENT DOCUMENTS

DE  10133572  4/2002
EP  0304538  3/1989
(Continued)

OTHER PUBLICATIONS

Official Action Dated Jul. 7, 2010 From the U.S. Patent and Trademark Office Re.: U.S. Appl. No. 10/597,675.
(Continued)

*Primary Examiner* — Christopher D Koharski
*Assistant Examiner* — Frances Oropeza (57) ABSTRACT

Apparatus for rehabilitating a patient who has a paretic body part, the apparatus comprising: a) at least one electromyograph (EMG) sensor adapted to being applied to a voluntary muscle of a healthy body part of the same type as the paretic body part, which at least one sensor produces at least one EMG signal; b) a neuromuscular electrical stimulation (NMES) device adapted for stimulating at least one voluntary muscle of the paretic body part; and c) a controller which controls the NMES device, making the amplitude of stimulation of the paretic body part at least partly dependent on the EMG signal from the healthy body part.

32 Claims, 5 Drawing Sheets

(56) References Cited

U.S. PATENT DOCUMENTS

| | | | |
|---|---|---|---|
| 3,919,691 A | 11/1975 | Noll | |
| 3,929,462 A | 12/1975 | Karmin | |
| 4,099,697 A | 7/1978 | Von Schuckmann | |
| 4,499,900 A | 2/1985 | Petrofsky et al. | |
| 4,582,049 A | 4/1986 | Ylvisaker | |
| 4,685,928 A | 8/1987 | Yaeger | |
| 4,691,694 A | 9/1987 | Boyd et al. | |
| 4,724,842 A | 2/1988 | Charters | |
| 4,765,610 A | 8/1988 | Sidwell | |
| 4,773,398 A | 9/1988 | Tatom | |
| 4,824,104 A | 4/1989 | Bloch | |
| 4,883,067 A | 11/1989 | Knispel et al. | |
| 4,921,244 A | 5/1990 | Berroth | |
| 4,936,299 A | 6/1990 | Erlandson | |
| 4,966,413 A | 10/1990 | Palarski | |
| 5,048,826 A | 9/1991 | Ryan | |
| 5,070,873 A | 12/1991 | Graupe et al. | |
| 5,158,074 A | 10/1992 | Grellas | |
| 5,179,939 A | 1/1993 | Donovan et al. | |
| 5,193,539 A | 3/1993 | Schulman et al. | |
| 5,193,540 A | 3/1993 | Schulman et al. | |
| 5,201,772 A | 4/1993 | Maxwell | |
| 5,211,161 A | 5/1993 | Stef | |
| 5,231,998 A | 8/1993 | Rosen et al. | |
| 5,244,441 A | 9/1993 | Dempster et al. | |
| 5,269,318 A | 12/1993 | Nashner | |
| 5,282,460 A | 2/1994 | Boldt | |
| 5,311,880 A | 5/1994 | Lancaster et al. | |
| 5,312,439 A | 5/1994 | Loeb | |
| 5,324,316 A | 6/1994 | Schulman et al. | |
| 5,343,856 A | 9/1994 | Proctor | |
| 5,358,251 A | 10/1994 | Ashton | |
| 5,391,128 A | 2/1995 | DeBear | |
| 5,397,865 A | 3/1995 | Park | |
| 5,405,367 A | 4/1995 | Schulman et al. | |
| 5,411,044 A | 5/1995 | Andolfi | |
| 5,413,611 A | 5/1995 | Haslam, II et al. | |
| 5,454,774 A | 10/1995 | Davis | |
| 5,466,213 A | 11/1995 | Hogan et al. | |
| 5,476,103 A | 12/1995 | Nahsner | |
| 5,476,428 A | 12/1995 | Potash et al. | |
| 5,616,104 A | 4/1997 | Mulenburg et al. | |
| 5,662,693 A | 9/1997 | Johnson et al. | |
| 5,690,389 A | 11/1997 | Ekman et al. | |
| 5,755,645 A | 5/1998 | Miller et al. | |
| 5,830,160 A | 11/1998 | Reinkensmeyer | |
| 5,836,304 A | 11/1998 | Kellinger et al. | |
| 5,846,086 A | 12/1998 | Bizzi et al. | |
| 5,853,353 A | 12/1998 | Blümel | |
| 5,919,115 A | 7/1999 | Horowitz et al. | |
| 5,954,621 A | 9/1999 | Jourtas et al. | |
| 5,980,435 A | 11/1999 | Joutras et al. | |
| 6,004,244 A | 12/1999 | Simonson | |
| 6,035,465 A | 3/2000 | Rogozinski | |
| 6,051,017 A | 4/2000 | Loeb et al. | |
| 6,057,828 A | 5/2000 | Rosenberg et al. | |
| 6,061,004 A | 5/2000 | Rosenberg et al. | |
| 6,064,912 A | 5/2000 | Kenney | |
| 6,246,200 B1 | 6/2001 | Blumenkranz et al. | |
| 6,270,445 B1 | 8/2001 | Dean, Jr. et al. | |
| 6,354,945 B1 | 3/2002 | Furuki et al. | |
| 6,379,393 B1 | 4/2002 | Mavroidis et al. | |
| 6,478,721 B1 | 11/2002 | Hunter | |
| 6,558,304 B1 | 5/2003 | Bardon et al. | |
| 6,592,315 B2 | 7/2003 | Osborne, Jr. | |
| 6,613,000 B1 | 9/2003 | Reinkensmeyer et al. | |
| 6,645,126 B1 | 11/2003 | Martin et al. | |
| 6,682,351 B1 | 1/2004 | Abraham-Fuchs et al. | |
| 6,774,885 B1 | 8/2004 | Even-Zohar | |
| 6,829,510 B2 | 12/2004 | Nathan et al. | |
| 6,839,594 B2 * | 1/2005 | Cohen et al. | 607/48 |
| 6,852,086 B2 | 2/2005 | Atlas et al. | |
| 6,870,438 B1 | 3/2005 | Shino et al. | |
| 6,966,882 B2 | 11/2005 | Horst | |
| 7,115,078 B1 | 10/2006 | Kalember et al. | |
| 7,163,488 B2 | 1/2007 | Anders et al. | |
| 7,209,788 B2 | 4/2007 | Nicolelis et al. | |
| 7,381,192 B2 | 6/2008 | Brodard et al. | |
| 7,504,577 B2 | 3/2009 | Riopelle | |
| 8,012,107 B2 | 9/2011 | Einav et al. | |
| 8,165,685 B1 * | 4/2012 | Knutson et al. | 607/48 |
| 2002/0064438 A1 | 5/2002 | Osborne, Jr. | |
| 2002/0094913 A1 | 7/2002 | Valentino | |
| 2003/0032524 A1 | 2/2003 | Lamar et al. | |
| 2003/0199370 A1 | 10/2003 | Bucay-Bissu | |
| 2003/0208109 A1 | 11/2003 | David et al. | |
| 2003/0208246 A1 * | 11/2003 | Kotlik et al. | 607/48 |
| 2004/0102723 A1 | 5/2004 | Horst | |
| 2004/0106881 A1 | 6/2004 | McBean et al. | |
| 2004/0172097 A1 | 9/2004 | Brodard et al. | |
| 2004/0180768 A1 | 9/2004 | Almada | |
| 2004/0245838 A1 | 12/2004 | Chiu | |
| 2005/0261114 A1 | 11/2005 | Heitzman et al. | |
| 2006/0149338 A1 | 7/2006 | Flaherty et al. | |
| 2006/0167564 A1 | 7/2006 | Flaherty et al. | |
| 2006/0229164 A1 | 10/2006 | Einav | |
| 2006/0277074 A1 | 12/2006 | Einav et al. | |
| 2006/0293617 A1 | 12/2006 | Einav et al. | |
| 2007/0282228 A1 | 12/2007 | Einav et al. | |
| 2007/0299371 A1 | 12/2007 | Einav et al. | |
| 2008/0132383 A1 | 6/2008 | Einav et al. | |
| 2008/0161733 A1 | 7/2008 | Einav et al. | |
| 2015/0141773 A1 | 5/2015 | Einav et al. | |

FOREIGN PATENT DOCUMENTS

| | | |
|---|---|---|
| EP | 0569489 | 11/1993 |
| EP | 0703752 | 4/1996 |
| EP | 0862930 | 9/1998 |
| EP | 1145682 | 10/2001 |
| EP | 1364636 | 11/2003 |
| FR | 2809615 | 12/2001 |
| GB | 2357848 | 7/2011 |
| JP | 59-160455 | 9/1984 |
| JP | 60-200312 | 10/1985 |
| JP | 61-071984 | 4/1986 |
| JP | 61-217174 | 9/1986 |
| JP | 61-265151 | 11/1986 |
| JP | 01-316815 | 12/1989 |
| JP | 02-102652 | 4/1990 |
| JP | 05-007608 | 1/1993 |
| JP | 05-026209 | 4/1993 |
| JP | 06-505407 | 6/1994 |
| JP | 07-163626 | 6/1995 |
| JP | 08-322189 | 12/1996 |
| JP | 08-511448 | 12/1996 |
| JP | 03-039345 | 4/1997 |
| JP | 09-173499 | 7/1997 |
| JP | 3044600 | 10/1997 |
| JP | 3048540 | 2/1998 |
| JP | 10-207624 | 8/1998 |
| JP | 11-009574 | 1/1999 |
| JP | 11-155836 | 6/1999 |
| JP | 11-253504 | 9/1999 |
| JP | 2000-102523 | 4/2000 |
| JP | 2000-112335 | 4/2000 |
| JP | 2000-279463 | 10/2000 |
| JP | 3126901 | 11/2000 |
| JP | 2001-204850 | 7/2001 |
| JP | 3081786 | 8/2001 |
| JP | 2001-299842 | 10/2001 |
| JP | 2002-065891 | 3/2002 |
| JP | 2002-126019 | 5/2002 |
| JP | 2002-127058 | 5/2002 |
| JP | 3087629 | 5/2002 |
| JP | 2002-263213 | 9/2002 |
| JP | 2002-351993 | 12/2002 |
| JP | 2003-093451 | 4/2003 |
| JP | 2003-164544 | 6/2003 |
| JP | 2003-190235 | 7/2003 |
| JP | 2004-008751 | 1/2004 |
| JP | 2004-174692 | 6/2004 |
| WO | WO 92/13504 | 8/1992 |
| WO | WO 98/37926 | 9/1998 |

(56) References Cited

FOREIGN PATENT DOCUMENTS

| | | |
|---|---|---|
| WO | WO 98/43700 | 10/1998 |
| WO | WO 98/43701 | 10/1998 |
| WO | WO 98/46127 | 10/1998 |
| WO | WO 02/13673 | 2/2002 |
| WO | WO 02/35457 | 5/2002 |
| WO | WO 02/092164 | 11/2002 |
| WO | WO 03/023546 | 3/2003 |
| WO | WO 2004/050172 | 6/2004 |
| WO | WO 2005/074369 | 8/2005 |
| WO | WO 2005/074370 | 8/2005 |
| WO | WO 2005/074371 | 8/2005 |
| WO | WO 2005/074372 | 8/2005 |
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2006/021952 | 3/2006 |
| WO | WO 2006/061834 | 6/2006 |
| WO | WO 2006/082584 | 8/2006 |

OTHER PUBLICATIONS

Translation of Notification of Reason for Rejection Dated Jul. 9, 2010 From the Japanese Patent Office Re. Application No. 2006-552014.
Response Dated Apr. 6, 2011 to Notification of Reasons for Rejection of Jan. 27, 2011 From the Japanese Patent Office Re. Application No. 2007-510233.
Response Dated Apr. 10, 2011 to Notification of Reasons for Rejection of Dec. 15, 2010 From the Japanese Patent Office Re. Application No. 2009-027772.
Backlife "The Backlife Idea", Product Information, <http://www.backlife.com>, 27 P., 2003.
Bak "The Complex Motion of Standing Still. Hydraulics, Sensors, and Human Modeling Dsta-Unified by Proprietary Software", <http://www.designnews.com/article/CA73202>, 5 P., 2001.
Burgar et al. "Development of Robots for Rehabilitation Therapy: The Palo Alto VA/Stanford Experience", Journal of Rehabilitation Research and Development, 37(6): 663-673, 2000.
Cameron et al. "Micromodular Implants to Provide Electrical Stimulation of Paralyzed Muscles and Limbs", IEEE Transactions on Biomedical Engineering, 44(9): 781-790, 1997. Abstract.
Graupe "EMG Pattern Analysis for Patient-Responsive Control of FES in Paraplegics for Walker-Supported Walking", IEEE Transactions on Biomedical Engineering, 36(7): 711-719, 1989. p. 711, 1-h Col., Paragraph 1-r-h Col., Paragraph 1, Figs.3, 5, p. 716, 1-h Col., Figs.
Messinger "ReAbility Games: Island Hunt Catch'em Patrol Muzment", Detailed Specifications Document, NOKs Technologies, Version 1.0, 16 P., 2004.
Micromedical "BalanceQuest: Computerized Dynamic Posturography", Micromedical Technologies, <http://www.micromedial.com>, 6 P., 2001.
Motek "Motek Medical Rehabilitation: Rehabilitation", <http://www.e-motek.com>, 1 P.
Peasgood et al. "EMG-Controlled Dosed Loop Electrical Stimulation Using a Digital Signal Processor", Electronics Letters, 36(22): 1832-1833, 2000. p. 1832, 1-h Col., Paragraph 1, Fig.1, p. 1833, r-h Col., Paragraph 1.
Richardson et al. "Comparing Smooth Arm Movement With the Two-Thirds Power Law and the Related Segmented-Control Hypothesis", The Journal of Neuroscience, 22(18): 8201-8211, 2002.
Viviani et al. "Minimum-Jerk, Two-Thirds Power Law, and Isochrony: Converging Approaches to Movement Planning", Journal of Experimental Psychology: Human Perception and Performance, 17: 32-53, 1995. Abstract.
Viviani et al. "Trajectory Determines Movement Dynamics", The Journal of Neuroscience, 7: 431-437, 1982.
Translation of Notification of Reason for Rejection Dated Aug. 13, 2010 From the Japanese Patent Office Re. Application No. 2006-552009.
Pfurtscheller et al. "Brain Oscillations Control Hand Orthosis in a Tetraplegic", Neuroscience Letters, 292: 211-214, 2000.
Response Dated Nov. 1, 2010 to Decision of Rejection of Jul. 9, 2010 From the Japanese Patent Office Re. Application No. 2006-552015.
Response Dated Dec. 6, 2010 to Official Action of Jul. 7, 2010 From the US Patent and Trademark Office Re.: U.S. Appl. No. 10/597,675.
Translation of Decision of Rejection Dated Jul. 9, 2010 From the Japanese Patent Office Re. Application No. 2006-552015.
Translation of Official Decision of Rejection Dated Oct. 29, 2010 From the Japanese Patent Office Re. Application No. 2007-529131.
Translation of Decision of Rejection Dated Feb. 1, 2011 From the Japanese Patent Office Re. Application No. 2006-552013.
Translation of Notification of Reason for Rejection Dated Feb. 3, 2011 From the Japanese Patent Office Re. Application No. 2006-552009.
Translation of Notification of Reasons for Rejection Dated Jan. 27, 2011 From the Japanese Patent Office Re. Application No. 2007-510233.
Translation of Notification of Reasons for Rejection Dated Dec. 15, 2010 From the Japanese Patent Office Re. Application No. 2009-027772.
Examination Report Dated Oct. 23, 2008 From the Instituto Mexicano de la Propriedad Industrial Re.: Application No. PA/a/2006/008919.
International Preliminary Report on Patentability Dated May 11, 2006 From the International Preliminary Examining Authority Re.: Application No. PCT/IL2005/000137.
International Preliminary Report on Patentability Dated Jan. 23, 2006 From the International Preliminary Examining Authority Re.: Application No. PCT/IL2005/000135.
International Search Report and the Written Opinion Dated Sep. 6, 2006 From the International Searching Authority Re.: Application No. PCT/IL05/01318.
International Search Report and the Written Opinion Dated May 12, 2006 From the International Searching Authority Re.: Application No. PCT/IL05/00136.
International Search Report and the Written Opinion Dated Jul. 17, 2006 From the International Searching Authority Re.: Application No. PCT/IL05/00142.
International Search Report Dated Jun. 2, 2005 From the International Searching Authority Re.: Application No. PCT/IL2005/000139.
International Search Report Dated Feb. 3, 2006 From the International Searching Authority Re.: Application No. PCT/IL05/00140.
International Search Report Dated Jun. 8, 2006 From the International Searching Authority Re.: Application No. PCT/IL05/00906.
International Search Report Dated Nov. 17, 2005 From the International Searching Authority Re.: Application No. PCT/IL2005/000137.
International Search Report Dated Aug. 24, 2005 From the International Searching Authority Re.: Application No. PCT/IL2005/000442.
International Search Report Dated Nov. 28 2005 From the International Search Authority Re.: Application No. PCT/IL2005/00141.
International Searching Report Dated Jun. 3, 2005 From the International Searching Authority Re.: Application No. PCT/IL2005/000135.
Official Action Dated Feb. 7, 2008 From the US Patent and Trademark Office Re.: U.S. Appl. No. 11/389,773.
Official Action Dated May 19, 2008 From the US Patent and Trademark Office Re.: U.S. Appl. No. 11/207,655.
Official Action Dated Jul. 26, 2007 From the US Patent and Trademark Office Re.: U.S. Appl. No. 11/389,773.
Official Action Dated Sep. 30, 2008 From the US Patent and Trademark Office Re.: U.S. Appl. No. 11/207,655.
Supplementary Partial European Search Report Dated Jan. 29, 2008 From the European Patent Office Re.: Application No. 05774725.5.
Translation of Notification of Reasons of Rejection Dated Jun. 12, 2009 From the Japanese Patent Office Re.: Application No. 2006-552011.
Translation of Notification of Reasons of Rejection Dated Sep. 14, 2009 From the Japanese Patent Office Re.: Application No. 2006-552014.

(56) References Cited

OTHER PUBLICATIONS

Written Opinion Dated Jun. 2, 2005 From the International Searching Authority Re.: Application No. PCT/IL2005/000139.
Written Opinion Dated Feb. 3, 2006 From the International Searching Authority Re.: Application No. PCT/IL05/00140.
Written Opinion Dated Jun. 3, 2005 From the International Searching Authority Re.: Application No. PCT/IL2005/000135.
Written Opinion Dated Jun. 8, 2006 From the International Searching Authority Re.: Application No. PCT/IL05/00906.
Written Opinion Dated Nov. 17, 2005 From the International Searching Authority Re.: Application No. PCT/IL2005/000137.
Written Opinion Dated Oct. 17, 2005 From the international Searching Authority Re.: Application No. PCT/IL05/00138.
Written Opinion Dated Aug. 24, 2005 From the International Searching Authority Re.: Application No. PCT/IL2005/000442.
Written Opinion Dated Nov. 28, 2005 From the International Searching Authority Re.: Application No. PCT/IL05/00141.
Russo "An Other Reality", Maariv, p. 14, Oct. 26, 2004. Hebrew Only!
Official action dated Sep. 14, 2010 from the US patent and trademark office re. U.S. Appl. No. 10/597,756.
Response dated Sep. 27, 2010 to notification of reasons for rejection of Jul. 12, 2010 from the Japanese patent office re. Application No. 2006-215045.
Response dated Aug. 4, 2010 to notification of reasons of rejection of Mar. 9, 2010 from the Japanese patent office re.: application No. 2006-552008.
Response dated Sep. 20, 2010 to notice of reason for rejection of Jun. 4, 2010 from the Japanese patent office re. Application No. 2007-529131.
Response dated Sep. 22, 2010 to notification of reasons of rejection of May 26, 2010 from the Japanese patent office re. Application No. 2006-552013.
Response dated Sep. 26, 2010 to notification of reason for rejection of Jul. 9, 2010 from the Japanese patent office re. Application No. 2006-552014.
Response dated Sep. 27, 2010 to official action of Jun. 28, 2010 from the us patent and trademark office re.: U.S. Appl. No. 11/568,463.
Translation of notification of reasons for rejection dated Jul. 12, 2010 from the Japanese patent office re. Application No. 2006-215045.
Official Action Dated Jun. 28, 2010 From the US Patent and Trademark Office Re.: U.S. Appl. No. 11/568,463.
Translation of Notification of Reasons of Rejection Dated May 26, 2010 From the Japanese Patent Office Re. Application No. 2006-552013.
Translation of Notice of Reason for Rejection Dated Jun. 4, 2010 From the Japanese Patent Office Re. Application No. 2007-529131.
Communication Pursuant to Article 96(2) Dated Dec. 11, 2006 From the European Patent Office Re.: Application No. 05703180.9.
Examination Report Dated Oct. 29, 2008 From the Instituto Mexicano de la Propriedad industrial Re.: Application No. PA/a2006/008914.
International Preliminary Report on Patentability Dated Aug. 16, 2007 From the International Bureau of WIPO Re.: Application No. PCT/IL2006/000140.
International Preliminary Report on Patentability Dated Jan. 19, 2007 From the International Preliminary Examining Authority Re.: Application No. PCT/IL05/00138.
International Preliminary Report on Patentability Dated Apr. 26, 2007 From the International Bureau of WIPO Re.: Application No. PCT/IL2005/000139.
International Preliminary Report on Patentability Dated Sep. 29, 2008 From the International Preliminary Examining Authority Re.: Application No. PCT/IL06/00140.
International Search Report and the Written Opinion Dated Jan. 3, 2007 From the International Searching Authority Re.: Application No. PCT/IL06/00140.
Office Action Dated Sep. 26, 2008 From the State Intellectual Properety Office of the People's Republic of China Re.: Application No. 205800103914.

Official Action Dated Oct. 1, 2008 From the US Patent and Trademark Office Re.: U.S. Appl. No. 11/389,773.
Communication of Results From Examination Dated Oct. 23, 2008 From the Instituto Mexicano de la Propriedad Industrial Re.: Application No. PA/a/2006/008914 and its Translation into English.
Communication Pursuant to Article 94(3) EPC Dated Oct. 12, 2009 From the European Patent Office Re.: Application No. 06704564.1.
International Preliminary Report on Patentability Dated Mar. 8, 2007 From the International Bureau of WIPO Re.: Application No. PCT/IL2005/000906.
International Preliminary Report on Patentability Dated Jun. 12, 2006 From the International Preliminary Examining Authority Re.: Application No. PCT/IL2005/000442.
International Preliminary Report on Patentability Dated Aug. 17, 2006 From the International Bureau of WIPO Re.: Application No. PCT/IL2005/000136.
International Preliminary Report on Patentability Dated Aug. 17, 2006 From the International Bureau of WIPO Re.: Application No. PCT/IL2005/000140.
International Preliminary Report on Patentability Dated Aug. 17, 2006 From the International Bureau of WIPO Re.: Application No. PCT/IL2005/000141.
International Preliminary Report on Patentability Dated Jun. 21, 2007 From the International Bureau of WIPO Re.: Application No. PCT/IL2005/001318.
Notification of Reasons of Rejection Dated Jun. 4, 2009 From the Japanese Patent Office Re.: Application No. 2006-552011.
Notification of Reasons of Rejection Dated Sep. 14, 2009 From the Japanese Patent Office Re.: Application No. 2006-552015 and its Translation Into English.
Official Action Dated Dec. 18, 2009 From the US Patent and Trademark Office Re.: U.S. Appl. No. 11/348,128.
Official Action Dated Mar. 19, 2010 From the US Patent and Trademark Office Re.: U.S. Appl. No. 10/597,675.
Official Action Dated May 19, 2009 From the US Patent and Trademark Office Re.: U.S. Appl. No. 11/792,477.
Official Action Dated Oct. 23, 2008 From the Instituto Mexicano de la Propriedad Industrial, Divisional Direction of Patents Re.: Application No. PA/a/2006/008919 and its Translation Into English.
Official Action Dated Jun. 24, 2009 From the US Patent and Trademark Office Re.: U.S. Appl. No. 11/207,655.
Response Dated Feb. 7, 2010 to Notification of Reasons of Rejection Dated Sep. 14, 2009 From the Japanese Patent Office Re.: Application No. 2006-552015.
Response Dated Feb. 9, 2010 to Notification of Reasons of Rejection of Sep. 14, 2009 From the Japanese Patent Office Re.: Application No. 2006-552014.
Response Dated Apr. 13, 2010 to Communication Pursuant to Article 94(3) EPC of Oct. 12, 2009 From the European Patent Office Re.: Application No. 06704564.1.
Translation of Office Action Dated Jan. 21, 2009 From the Japanese Patent Office Re.: Application No. 2006-552008.
Response Dated Apr. 19, 2010 to Official Action of Mar. 19, 2010 From the US Patent and Trademark Office Re.: U.S. Appl. No. 10/597,675.
Supplementary Partial European Search Report and the European Search Opinion Dated Jul. 14, 2009 From the European Patent Office Re.: Application No. 06704564.1.
International Preliminary Report on Patentability Dated Apr. 21, 2010 From the International Preliminary Examining Authority Re.: Application No. PCT/IL05/00138.
Official Action Dated May 9, 2011 From the US Patent and Trademark Office Re.: U.S. Appl. No. 11/568,463.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar. 9, 2010 From the Japanese Patent Office Re.: Application No. 2006-552008.
Response Dated Feb. 22, 2011 to Official Decision of Rejection of Oct. 29, 2010 From the Japanese Patent Office Re. Application No. 2007-529131.

(56) References Cited

OTHER PUBLICATIONS

Notice of Allowance Dated Feb. 16, 2011 From the US Patent and Trademark Office Re.: U.S. Appl. No. 10/597,675.
Translation of Notification of Reason for Rejection Dated Apr. 7, 2011 From the Japanese Patent Office Re. Application No. 2006-552014.
Translation of Notification of Reasons for Rejection Dated Apr. 6, 2011 From the Japanese Patent Office Re. Application No. 2006-215045.
Official Action Dated Mar. 16, 2011 From the US Patent and Trademark Office Re.: U.S. Appl. No. 11/568,463.
Response Dated Jun. 14, 2011 to Notification of Reason for Rejection of Feb. 3, 2011 From the Japanese Patent Office Re. Application No. 2006-552009.
Translation of Decision of Rejection Dated Jun. 30, 2011 From the Japanese Patent Office Re. Application No. 2007-510233.
Translation of Notification of Reasons of Rejection Dated Jul. 4, 2011 From the Japanese Patent Office Re. Application No. 2006-552013.
Response Dated Jul. 6, 2011 to the Notification of Reasons for Rejection of Apr. 6, 2011 From the Japanese Patent Office Re. Application No. 2006-215045.
Response Dated Jun. 9, 2011 to Official Action of May 9, 2011 From the US Patent and Trademark Office Re.: U.S. Appl. No. 11/568,463.
Response Dated Jul. 12, 2011 to Official Action of Jun. 15, 2011 From the US Patent and Trademark Office Re. U.S. Appl. No. 10/597,671.
Response Dated Jul. 18, 2011 to Official Action of Mar. 16, 2011 From the US Patent and Trademark Office Re.: U.S. Appl. No. 11/568,463.
Response Dated Aug. 9, 2011 to Questioning of May 25, 2011 From the Japanese Patent Office Re. Application No. 2006-552015.
Official Action Dated Aug. 10, 2011 From the US Patent and Trademark Office Re. U.S. Appl. No. 10/597,633.
Examination Report Dated Aug. 25, 2011 From the Government of India, Patent Office Intellectual Property Building Re.: Application No. 3230/CHENP/2006.
Examination Report Dated Aug. 25, 2011 From the Government of India, Patent Office, Intellectual Property Building Re. Application No. 3232/CHENP/2006.
Response Dated Aug. 24, 2011 to Notification of Reasons for Rejection of Jun. 6, 2011 From the Japanese Patent Office Re. Application No. 2009-027772.
Notice of Reasons for Rejection Dated Aug. 31, 2011 From the Japanese Patent Office Re. Application No. 2006-552009 and its Translation Into English.
Official Action Dated Sep. 1, 2011 From the US Patent and Trademark Office Re.: U.S. Appl. No. 11/660,965.
Official Action Dated Sep. 1, 2011 From the US Patent and Trademark Office Re.: U.S. Appl. No. 11/568,463.
Official Action Dated Sep. 23, 2011 From the US Patent and Trademark Office Re. U.S. Appl. No. 10/597,671.
Response Dated Sep. 26, 2011 to Notification of Reasons of Rejection of Jul. 4, 2011 From the Japanese Patent Office Re. Application No. 2006-552013.
Response Dated Oct. 5, 2011 to Notification of Reason for Rejection of Apr. 7, 2011 From the Japanese Patent Office Re. Application No. 2006-552014.
Response Dated Oct. 10, 2011 to Official Action of Aug. 10, 2011 From the US Patent and Trademark Office Re. U.S. Appl. No. 10/597,633.
Official Action Dated Oct. 7, 2011 From the US Patent and Trademark Office Re.: U.S. Appl. No. 11/568,463.
Response Dated Nov. 9, 2011 to Notice of Reasons for Rejection of Aug. 31, 2011 From the Japanese Patent Office Re. Application No. 2006-552009.
Official Action Dated Nov. 15, 2011 From the US Patent and Trademark Office Re. U.S. Appl. No. 10/597,633.
Official Action Dated Jan. 17, 2012 From the US Patent and Trademark Office Re. U.S. Appl. No. 10/597,605.

Amendment Dated Oct. 28, 2011 in Response to Decision of Rejection Dated Jun. 30, 2011 From the Japanese Patent Office Re. Application No. 2007-510233.
Notice of Allowance Dated Dec. 23, 2011 From the US Patent and Trademark Office Re.: U.S. Appl. No. 11/883,663.
Notice of Appeal Dated Oct. 28, 2011 in Response to Decision of Rejection Dated Jun. 30, 2011 From the Japanese Patent Office Re. Application No. 2007-510233.
Translation of Notification of Reasons for Rejection Dated Dec. 21, 2011 From the Japanese Patent Office Re. Application No. 2006-552015.
Translation of Official Query Dated Dec. 16, 2011 From the Japanese Patent Office Re. Application No. 2007-529131.
Abe et al. "ICA. A Study of EEG Analysis Method Using ICA", Proceedings of the 1999 IEICE General Conference, p. 149, 1999.
Translation of Questioning Dated Jan. 13, 2012 From the Japanese Patent Office Re. Application No. 2006-552013.
Official Action Dated Oct. 1, 2008 From the US Patent Office Re.: U.S. Appl. No. 11/389,773.
Official Action Dated Jul. 22, 2008 From the US Patent Offcie Re.: U.S. Appl. No. 11/389,773.
Supplemental Notice of Allowability Dated Aug. 9, 2011 From the US Patent and Trademark Office Re.: U.S. Appl. No. 10/597,675.
Proceedings Further With the European Patent Applicaiton Pursuant to Rule 70(2) EPC Dated Feb. 23, 2012 From the European Patent Office Re. Application No. 05703181.7.
Supplementary European Search Report Dated Feb. 6, 2012 From the European Patent Office Re. Application No. 05703181.7.
Communication Pursuant to Article 94(3) EPC Dated Feb. 8, 2012 From the European Patent Office Re. Application No. 05703179.1.
Invitation Pursuant to Rule 62a(1) EPC and Rule 63(1) EPC Dated Mar. 20, 2012 From the European Patent Office Re. Application No. 05703183.3.
Notice of Allowance Dated Apr. 4, 2012 From the US Patent and Trademark Office Re. U.S. Appl. No. 10/597,599.
Invitation Pursuant to Rule 62a(1) EPC and Rule 63(1) EPC Dated Mar. 20, 2012 From the European Patent Office Re. Application No. 05703184.1.
Official Action Dated May 14, 2012 From the US Patent and Trademark Office Re. U.S. Appl. No. 10/597,633.
Invitation Pursuant to Rule 62a(1) and Rule 63(1) EPC Dated Mar. 20, 2012 From the European Patent Office Re. Application No. 05703185.8.
Official Action Dated Jan. 27, 2012 From the US Patent and Trademark Office Re. U.S. Appl. No. 10/597,605.
Communication Under Rule 71(3) EPC Dated Nov. 7, 2012 From the European Patent Office Re. Application No. 05703179.1.
Examination Report Dated Aug. 25, 2011 From the Government of India, Patent Office, Intellectual Property Building Re.: Application No. 3231/CHENP/2006.
International Search Report Dated Oct. 17, 2005 From the International Searching Authority Re.: Application No. PCT/IL05/00138.
Notice of Allowance Dated Oct. 19, 2011 From the Japanese Patent Office Re. Application No. 2006-215045 and its Translation Into English.
Official Action Dated Sep. 1, 2011 From the US Patent and Trademark Office Re.: U.S. Appl. No. 11/883,663.
Official Action Dated Sep. 7, 2012 From the US Patent and Trademark Office Re. U.S. Appl. No. 10/597,671.
Official Action Dated May 9, 2011 From the US Patent and Trademark Office Re.: U.S. Appl. No. 11/883,663.
Official Action Dated Jun. 15, 2011 From the US Patent and Trademark Office Re. U.S. Appl. No. 10/597,671.
Official Action Dated Oct. 17, 2012 From the US Patent and Trademark Office Re. U.S. Appl. No. 10/597,635.
Official Action Dated Dec. 29, 2008 From the US Patent and Trademark Office Re.: U.S. Appl. No. 11/792,477.
Response Dated Jun. 9, 2011 to Official Action of May 9, 2011 From the US Patent and Trademark Office Re.: U.S. Appl. No. 11/883,663.
Weiskopf et al. "Principles of a Brain-Computer Interface (BCI) Based on Real-Time Functional Magnetic Resonance Imaging (FMRI)", IEEE Transactions on Biomedical Engineering, 51(6): 966-970, Jun. 2004.

(56) References Cited

OTHER PUBLICATIONS

Yoo et al. "Brain-Computer Interface Using FMRI: Spatial Navigation by Thoughts", Clinical Neuroescience and Neuropathology, 15(10): 1591-1595, Jul. 19, 2004.
Official Action Dated Nov. 27, 2012 From the US Patent and Trademark Office Re. U.S. Appl. No. 10/597,633.
Official Action Dated Jul. 18, 2013 From the US Patent and Trademark Office Re. U.S. Appl. No. 10/597,633.
Applicant-Initiated Interview Summary Dated Dec. 20, 2013 From the US Patent and Trademark Office Re. U.S. Appl. No. 10/597,633.
Communication Pursuant to Article 94(3) EPC Dated May 13, 2014 From the European Patent Office Re. Application No. 06704564.1.
Official Action Dated Jun. 15, 2010 From the U.S. Patent and Trademark Office Re. U.S. Appl. No. 10/597,671.
Translation of Notification of Reasons for Rejection Dated Jun. 6, 2011 From the Japanese Patent Office Re. Application No. 2009-027772.
Official Action Dated Mar. 19, 2012 From the US Patent and Trademark Office Re. U.S. Appl. No. 10/597,635.
Communication Pursuant to Article 94(3) EPC Dated Mar. 19, 2013 From the European Patent Office Re. Application No. 05703183.3.
Communication Pursuant to Article 94(3) EPC Dated Mar. 19, 2013 From the European Patent Office Re. Application No. 05703184.1.
Communication Pursuant to Article 94(3) EPC Dated Mar. 19, 2013 From the European Patent Office Re. Application No. 05703185.8.
Official Action Dated Mar. 19, 2014 From the US Patent and Trademark Office Re. U.S. Appl. No. 11/660,965.
Official Action Dated Sep. 26, 2013 From the US Patent and Trademark Office Re. U.S. Appl. No. 10/597,635.
Official Action Dated Jan. 16, 2014 From the US Patent and Trademark Office Re. U.S. Appl. No. 10/597,635.
Official Action Dated Apr. 10, 2014 From the US Patent and Trademark Office Re. U.S. Appl. No. 10/597,605.
Translation of Notification of Names of Appeal Examiners and Appeal Clerk Dated Jun. 6, 2012 From the Japanese Patent Office Re. Application No. 2006-552013.
Applicant-Initiated Interview Summary Dated Jan. 23, 2013 From the US Patent and Trademark Office Re. U.S. Appl. No. 10/597,671.
Applicant-Initiated Interview Summary Dated Feb. 6, 2013 From the US Patent and Trademark Office Re. U.S. Appl. No. 10/597,635.
Notice of Allowance Dated Jun. 10, 2013 From the US Patent and Trademark Office Re. U.S. Appl. No. 10/597,671.
Translation of Questioning Dated May 25, 2011 From the Japanese Patent Office Re. Application No. 2006-552015.
Advisory Action Before the Filing of an Appeal Brief Dated Jul. 26, 2012 From the US Patent and Trademark Office Re. U.S. Appl. No. 10/597,633.
Applicant-Initiated Interview Summary Dated Jun. 11, 2012 From the US Patent and Trademark Office Re. U.S. Appl. No. 10/597,633.
Communication Pursuant to Article 94(3) EPC Dated Jul. 3, 2012 From the European Patent Office Re. Application No. 05703181.7.
Official Action Dated Aug. 1, 2012 From the US Patent and Trademark Office Re.: U.S. Appl. No. 10/597,605.
Official Action Dated Jun. 14, 2012 From the US Patent and Trademark Office Re.: U.S. Appl. No. 11/660,965.
Proceeding Further With the European Patent Application Pursuant to Rule 70(2) EPC Dated Jul. 30, 2012 From the European Patent Office Re. Application No. 05703185.8.
Proceedings Further With the European Patent Application Pursuant to Rule 70(2) EPC Dated Jul. 30, 2012 From the European Patent Office Re. Application No. 05703183.3.
Proceedings Further With the European Patent Application Pursuant to Rule 70(2) EPC Dated Jul. 30, 2012 From the European Patent Office Re. Application No. 05703184.1.
Supplementary Partial European Search Report Dated Jul. 11, 2012 From the European Patent Office Re. Application No. 05703183.3.
Supplementary Partial European Search Report Dated Jul. 11, 2012 From the European Patent Office Re. Application No. 05703184.1.
Supplementary Partiel European Search Report Dated Jul. 11, 2012 From the European Patent Office Re. Application No. 05703185.8.
Response Dated Dec. 1, 2011 to Official Action of Sep. 1, 2011 From the US Patent and Trademark Office Re.: U.S. Appl. No. 11/883,663.
Official Action Dated Dec. 7, 2011 From the US Patent and Trademark Office Re.: U.S. Appl. No. 11/660,965.
Restriction Official Action Dated Dec. 12, 2011 From the US Patent and Trademark Office Re. U.S. Appl. No. 10/597,635.
Harwin et al. "Clinical Potential and Design of Programmable Mechanical Impedances for Orthotic Applications", Robotica, 16: 523-530, 1998.
Communication Pursuant to Article 94(3) EPC Dated Sep. 29, 2014 From the European Patent Office Re. Application No. 06704564.1.
Applicant-Initiated Interview Summary Dated Aug. 1, 2014 From the US Patent and Trademark Office Re. U.S. Appl. No. 10/597,605.
Communication Pursuant to Article 94(3) PC Dated Jul. 17, 2014 From the European Patent Office Re. Application No. 05703181.7.
Communication Pursuant to Article 94(3) EPC Dated Jul. 28, 2014 From the European Patent Office Re. Application No. 05703183.3.
Communication Pursuant to Article 94 (3) EPC Dated Jul. 28, 2014 From the European Patent Office Re. Application No. 05703184.1.
Communication Pursuant to Article 94(3) EPC Dated Jul. 28, 2014 From the European Patent Office Re. Application No. 05703185.8.
Kristy et al. "A Robotic Arm 'Smart Exercise System': A Rehabilitation Therapy Modality", Engineering in Medicine and Biology Society, Proceedings of the Annual International Conference of the IEEE Engineering in Images of the Twenty-First Century, XP010088537, p. 1504-1505, 1989.
Martens et al. "A FRIEND for Assisting Handicapped People. The Semiautonomous Robotic System 'FRIEND' Consists of an Electric Wheelchair With a Robotic Arm and Utilizes a Speech Interface", IEEE Robotics & Automation Magazine, XP055130671, 8(1): 57-65, Mar. 1, 2001.

* cited by examiner

NEUROMUSCULAR STIMULATION

RELATED APPLICATIONS

The present application is a US National Phase Application of PCT Application No. PCT/IL2005/000135, filed on Feb. 4, 2005. This application also claims the benefit under 119(e) of U.S. Provisional Application No. 60/542,022, filed on Feb. 5, 2004, and U.S. Provisional Application 60/566,078 filed on Apr. 29, 2004, the disclosure of both applications are incorporated herein by reference. This application is also related to PCT applications, being filed on Feb. 4, 2005 and by the same applicant as the present application, and having application numbers: PCT/IL2005/000138; PCT/IL2005/000137; PCT/IL2005/000139; PCT/IL2005/000136; PCT/IL2005/000142; PCT/IL2005/000140; and PCT/IL2005/000141. The disclosures of all these applications are incorporated herein by reference.

FIELD OF THE INVENTION

The field of the invention is devices for rehabilitation of patients with motor control problems.

BACKGROUND OF THE INVENTION

Voluntary muscle movement is caused by electrical impulses which originate in the somato-motor cortex of the brain. A neuron in the somato-motor cortex sends electrical signals to a motor neuron in the spinal cord, which in turn sends electrical signals which stimulate the contraction of muscle fibers, producing movement. All of the muscle fibers which are stimulated by a given motor neuron are called a "motor unit." Each muscle fiber exhibits an electrical potential across its cell membrane, which changes when the muscle contracts.

In electromyography (EMG), the difference in potential on the surface of the skin is measured between the center and the ends of a muscle, which gives a measure of the number of contracting muscle fibers. EMG is regularly used to diagnose a variety of medical conditions in patients, as well as in healthy subjects for research on muscle function.

In stroke patients with damage to their somato-motor cortex, electrical signals are not generated for one or more muscles or parts of muscles, or do not reach those muscles, and normal contraction of those muscles is impossible. Often, residual EMG signals, too weak or too spread out to cause the muscles to contract, are still detectable.

Neuromuscular electrical stimulation (NMES) is used to produce contraction of a muscle which cannot contract normally in a stroke patient. NMES may stop spasticity in a muscle, and may prevent the muscle from atrophying. It is also known to turn NMES of a single muscle on or off in response to residual EMG signals detected from that muscle, thereby allowing the muscle to contract under the control of the patient.

SUMMARY OF THE INVENTION

An aspect of an embodiment of the invention concerns applying NMES to a paretic arm, or any other part of the body with voluntary muscles, in a manner which is insufficient to cause a desired motion. In an exemplary embodiment of the invention, the desired motion is provided or assisted by an actuator which moves or helps move the paretic portion. Alternatively or additionally, a patient provides the required additional neural signals (e.g., via natural pathways). In some embodiments the actuating device is used to resist motion and/or to guide the motion to a desired pathway. Optionally, a controller is provided storing thereon a plurality of desired motions and expected responses by the patient to various stimulation and assistance levels.

In an exemplary embodiment of the invention, the NMES is provided at an amplitude that would be too low to produce motion by itself, but which, in combination with nerve impulses arising in the patient's motor cortex, allow the arm or other body part to move, or to move more effectively than without the NMES. It does this, for example, by producing muscular feedback which helps to train the motor cortex to move that body part. In some embodiments, the NMES need not be very strong, or very precisely directed, in order to do this. Whenever this application refers to arms, it should be understood that any other body part, or combination of body parts, with voluntary muscles may be used instead. Optionally, EMG signals from the same arm, or from the corresponding muscles in the patient's other arm, or from the arm of another person, are used to determine the pattern (e.g., timing and/or amplitude) of the NMES.

Another aspect of an embodiment of the invention concerns the use of EMG signals from one arm, optionally a healthy arm, undergoing voluntary motion, to determine a pattern of NMES to be applied to another, paretic arm. Optionally EMG signals from the paretic arm are also used, at least to determine the timing of the NMES. Optionally, the healthy arm is the other arm of the patient, and the patient tries to move both arms in synchrony, in a mirror symmetric pattern.

Optionally, for either of these embodiments of the invention, the EMG and NMES involve a coordinated sequence of contractions of more than one muscle, and/or a range of amplitudes for the NMES, rather than having the NMES either on or off for a single muscle.

By providing feedback, through the kinesthetic sense, of a coordinated sequence of muscle contractions, the patient's nervous system may be encouraged to utilize alternative undamaged pathways for nerve impulses, or alternative locations in the motor cortex, and the patient can learn to move his arm more effectively on his own. This may be especially true if the NMES is coordinated with the weak nerve impulses that the patient produces on his own, as measured by the EMG.

Optionally, a device, for example a robotic arm, which monitors and displays the movement of the arm, is used for the paretic arm, and optionally also for the healthy arm if one is used. Information about the movement of the arm can provide further feedback to the patient, as well as feedback for controlling the NMES, and feedback to a physical therapist who is monitoring the progress of the patient's rehabilitation. A robotic arm or similar device can also mechanically move the paretic arm, complementing the NMES by providing a different kind of kinesthetic feedback. A robotic arm can also exert a force working against the muscle, providing a way to strengthen the arm as well as to measure progress in strengthening the arm.

There is thus provided in accordance with an exemplary embodiment of the invention, apparatus for rehabilitating a patient who has a paretic body part, the apparatus comprising:
   a) at least one electromyography (EMG) sensor adapted to being applied to a voluntary muscle of a healthy body part of the same type as the paretic body part, which at least one sensor produces at least one EMG signal;
   b) a neuromuscular electrical stimulation (NMES) device adapted for stimulating at least one voluntary muscle of the paretic body part;

c) a controller which controls the NMES device and expects a motion of the paretic body part, making the amplitude of stimulation of the paretic body part at least partly dependent on the EMG signal from the healthy body part such that said NMES stimulation is not sufficient, on its own, to move said paretic body part said expected motion.

Optionally, the at least one muscle of the healthy body part corresponds to the at least one muscle of the paretic body part.

In an exemplary embodiment of the invention, said controller is configured to process said EMG signals and determine at least one property of said NMES signal.

In an exemplary embodiment of the invention, the controller is configured so that the NMES stimulates the paretic body part to make a movement corresponding to a movement made by the healthy body part when the EMG signals are sensed. Optionally, the controller is configured so that the amplitude of stimulation of at least one of the at least one muscle of the paretic body part increases when the EMG signal from the corresponding muscle of the healthy body part increases at a corresponding time in the movement of the healthy body part.

In an exemplary embodiment of the invention, the at least one muscle of the paretic body part comprises an antagonistic pair of muscles, and the controller is configured so that the amplitude of stimulation of one muscle of the antagonistic pair of muscles decreases when the EMG signal from the muscle in the healthy body part corresponding to the other muscle of the antagonistic pair of muscles increases at a corresponding time in the movement of the healthy body part.

In an exemplary embodiment of the invention, one or both of the controller and the NMES device are configured so that the stimulation amplitude is not high enough to cause the stimulated muscle to contract in the absence of nerve impulses from the patient's brain, but is high enough to cause the muscle to contract in the presence of nerve impulses from the patient's brain, for at least some patients who cannot move said body part by themselves.

In an exemplary embodiment of the invention, the at least one EMG sensor comprises a plurality of EMG sensors, each EMG sensor adapted to being applied to a different muscle or muscle part of the healthy body part. Optionally, each EMG sensor produces a separate EMG signal. Optionally, the NMES device is adapted to independently stimulate a plurality of muscles or muscle parts of the paretic body part. Optionally, said plurality of muscles or muscle parts of the paretic body part correspond to the muscles or muscle parts of the healthy body part to which the plurality of EMG sensors are adapted to being applied. Optionally, the controller is configured so that amplitude of NMES stimulation of said plurality of muscles or muscle parts of the paretic body part is at least partly dependent on the EMG signals from the plurality of EMG sensors. Optionally, the controller is configured so that the amplitude of NMES stimulation of each of said plurality of muscles or muscle parts depends at least partly on the EMG signal from the corresponding muscle or muscle part.

In an exemplary embodiment of the invention, the paretic body part is a body part that comes in pairs. Optionally, the paretic body part is an arm. Alternatively or additionally, the paretic body part comprises a leg.

In an exemplary embodiment of the invention, the healthy body part belongs to the patient. Alternatively, the healthy body part belongs to a different person.

In an exemplary embodiment of the invention, the controller makes the stimulation amplitude at least partly dependent on a processed form of the EMG signal. Optionally, the processed form of the EMG signal is stretched out in time from the EMG signal. Alternatively or additionally, the processed form of the EMG signal corresponds to an EMG signal that would be produced by a movement of the healthy body part that is a mirror image of a movement that the healthy part was undergoing when the EMG signal was generated. Alternatively or additionally, the processed form of the EMG signal is time delayed from the EMG signal.

In an exemplary embodiment of the invention, the apparatus includes a first position sensing device which monitors a position of the healthy body part. Optionally, the apparatus includes a first actuating device which mechanically changes the position of the healthy body part.

In an exemplary embodiment of the invention, the apparatus includes a second position sensing device which monitors a position of the paretic body part.

In an exemplary embodiment of the invention, the apparatus includes a paretic actuating device which mechanically changes the position of the paretic body part under control of said controller and according to said expected move.

There is also provided in accordance with an exemplary embodiment of the invention apparatus adapted for rehabilitating a class of patients who have a paretic body part, the apparatus comprising a neuromuscular electrical stimulation (NMES) device adapted to stimulate at least one voluntary muscle in the paretic body, wherein the amplitude of stimulation is not sufficient by itself to cause contraction of said muscle, but the amplitude of stimulation is sufficient to cause contraction of said muscle when a patient in said class attempts to move the body part at the same time.

In an exemplary embodiment of the invention, the apparatus comprises at least one paretic EMG sensor adapted for applying to a voluntary muscle of the paretic body part, which at least one paretic EMG sensor produces at least one paretic EMG signal. Optionally, the controller makes the amplitude of stimulation of the paretic body part at least partly dependent on the at least one paretic EMG signal. Optionally, the at least one paretic EMG sensors adapted for applying to the paretic body part comprise a plurality of paretic EMG sensors, each adapted for being applied to a different muscle or muscle part of the paretic body part, and each producing a separate paretic EMG signal. Optionally, the NMES device is adapted to stimulate the muscles or muscle parts of the paretic body that the paretic EMG sensors are adapted for being applied to, and the controller is configured to make the amplitude of stimulation of each muscle or muscle part depend at least partly on the paretic EMG signal from that muscle or muscle part.

In an exemplary embodiment of the invention, said first actuating device mechanically changes the position of said healthy body part at varying levels chosen from the group of complete assistance, partial assistance or no assistance.

In an exemplary embodiment of the invention, said first actuating device mechanically changes the position of said healthy body part by limiting the range of motion of said part.

In an exemplary embodiment of the invention, said second actuating device mechanically changes the position of said paretic body part at varying levels chosen from the group of complete assistance, partial assistance or no assistance.

In an exemplary embodiment of the invention, said second actuating device mechanically changes the position of said paretic body part by limiting the range of motion of said part.

There is also provided in accordance with an exemplary embodiment of the invention, a method of rehabilitating a patient who has a paretic body part, the method comprising:

a) having the patient or another person move a healthy body part that is of the same type as the paretic body part;

b) detecting EMG signals from the healthy body part while it is being moved;
c) processing said EMG signals to determine at least one property of a NMES signal;
d) applying a NMES signal to the paretic body part, responsive to said processing; and
e) moving said paretic body part at most partially by said NEMS stimulation.

Optionally, said NMES is applied at a timing according to said EMG signals. Alternatively or additionally, said NMES is applied at an amplitude according to said EMG signals.

In an exemplary embodiment of the invention, the method comprises having the patient attempt to move the paretic body part, while the NMES is applied, in the same pattern of movement that the healthy body part is moved in while the EMG signals are detected. Optionally, detecting the EMC signals comprises detecting the EMG signals from a plurality of muscles or muscle parts of the healthy body part, and applying NMES comprises applying NMES to a plurality of muscles or muscle parts of the paretic body part corresponding to the plurality of muscles or muscle parts of the healthy body part. Optionally, the amplitude of NMES applied to each muscle or muscle part of the paretic body part during a time interval in the pattern of attempted movement of the paretic body part depends at least partly on the EMG signal detected from the corresponding muscle or muscle part of the healthy body, during a corresponding time interval in the pattern of movement of the healthy body part.

In an exemplary embodiment of the invention, the paretic body part is mechanically provided with movement by an actuating device. Optionally, said actuating device is synchronized to said detected EMG. Alternatively or additionally, said actuating device is synchronized to said applied NMES. Alternatively or additionally, the paretic body part is mechanically assisted with movement by an actuating device. Alternatively or additionally, movement of the paretic body part is limited by an actuating device.

BRIEF DESCRIPTION OF THE DRAWINGS

Exemplary embodiments of the invention are described in the following sections with reference to the drawings. The drawings are generally not to scale and the same or similar reference numbers are used for the same or related features on different drawings.

DETAILED DESCRIPTION OF EXEMPLARY EMBODIMENTS

Figure 1:
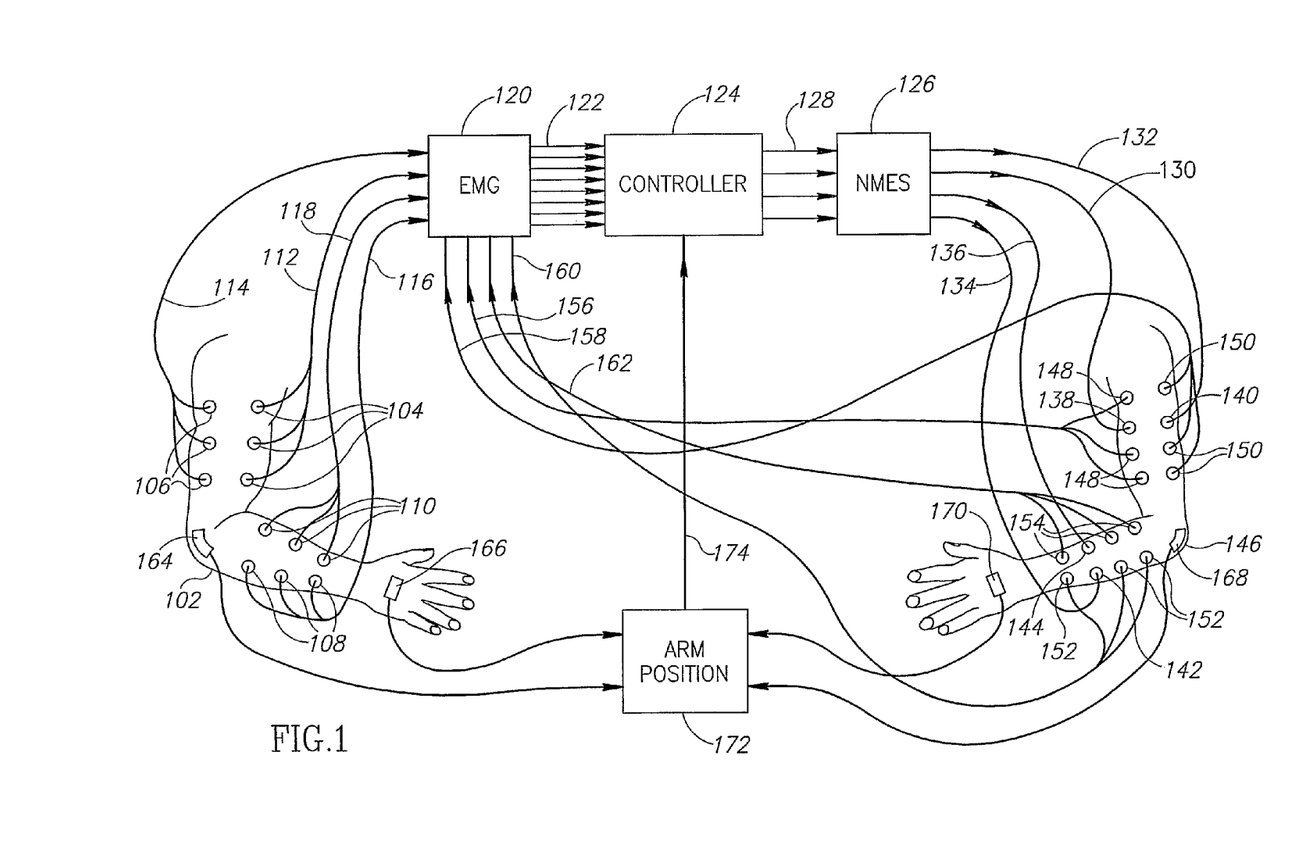
FIG. 1 is a schematic drawing of a healthy arm with EMG electrodes, an EMG unit, a signal processing unit, an NMES unit, and a paretic arm with NMES and EMG electrodes, according to an exemplary embodiment of the invention.

FIG. 1 shows an apparatus for applying NMES to several muscles of a paretic arm, guided by EMG signals from the corresponding muscles of a healthy arm. Healthy arm 102, belonging either to the patient with the paretic arm or to someone else, has EMG electrodes attached to the skin. The person whose arm it is moves the arm voluntarily in a particular pattern, which generates a certain time-dependent pattern of EMG voltages in the muscles. There are optionally four EMG channels, one channel measuring EMG signals from each of four muscles: the biceps, the triceps, the flexors, and the extensors. Each channel uses three electrodes, two recording signals from near each end of the muscle, and one reference electrode in the middle. For example, electrodes 104 measure the biceps, electrodes 106 measure the triceps, electrodes 108 measure the flexors, and electrodes 110 measure the extensors It should be understood from the description of the present invention that similar arrangements are optionally arranged for other muscle pair groups, such as the pectoralis major and deltoid pairs. When the arm is moved voluntarily, these electrodes transmit the EMG signals corresponding to the pattern of muscle contractions producing that movement of the arm, via cable bundles 112, 114, 116, and 118, to an EMG device 120. The EMG device, or a separate controller, does preliminary processing of the EMG signals, for example amplifying them, digitizing them, and/or recording them.

Figure 2:
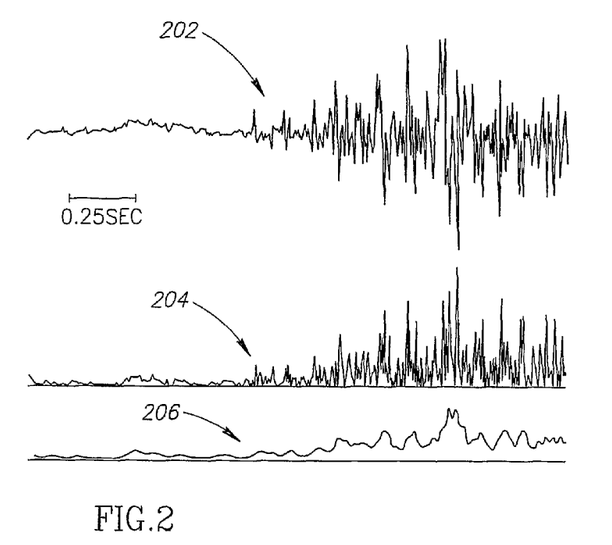
FIG. 2 shows plots of a raw EMG signal, rectified signal, smoothed rms signal, according to an exemplary-embodiment of the invention.

The EMG signals are then transmitted, via a cable 122, to a controller 124, which is, for example, a personal computer, or comprises special dedicated hardware. The controller optionally further processes the EMG signals, for example filtering them, rectifying them, smoothing them, changing the timing, or cutting and pasting parts of a sequence in a different order. The signal processing is optionally done automatically, or is partly or entirely under the control the physical therapist. FIG. 2 shows a plot of a filtered raw EMG signal 202 from one channel, a rectified signal 204, and a smoothed rectified signal 206, in which the root mean square of the signal is calculated in each of a sequence of time intervals, or example every 10 milliseconds. The smoothed rectified signal is a measure of the overall degree of contraction of the muscle or section of the muscle measured by that channel, while eliminating high frequency noise associated with the changes in potential of individual muscle fibers. Optionally, the smoothed rectified EMG signal is averaged over many repetitions of the same pattern of movement. Optionally, the EMG sensors add up or average the EMG signals coming from several different sections of the muscle, or this is done by the signal processing. An optional type of signal processing is validating EMG signals, for example, by measuring the actual motion of a healthy limb while measuring EMG thereon, so that it is clear that the EMG signals result from the desired movement. Optionally, one or more of the parameters of the signal processing are controlled by the therapist. In some embodiments of the invention, the smoothed rectified EMG signal is created by dispensing with anomalous EMG readings, such as not factoring the high and low readings, and averaging the rest of the readings over multiple repetitions. In some embodiments, the EMG is measured and the NMES applied, at a time delay, for example, to allow multiple EMG signals to be collected and averaged.

Controller 124 also controls NMES device 126, via cable 128. Optionally, controller 124 commands NMES device to produce NMES signals in each of four channels. The signals in the four channels travel through cables 130, 132, 134, and 136, to electrodes 138, 140, 142, and 144, which respectively stimulate the biceps, triceps, flexors, and extensors on the patient's paretic arm 146 (or optionally any other muscle pair as the case may be). Optionally, the NMES signals in each channel are given a time-dependent amplitude which will produce the same movement in the paretic arm as was performed by the healthy arm. This is done, for example, by making the signal strength in each NMES channel depend on the processed signal amplitude from a corresponding one of the four EMG channels. For example, the NMES signal is proportional to the processed EMG signal amplitude, or is a fixed monotonic function of the processed EMG signal amplitude, for the corresponding channel.

Optionally, the NMES signal depends also on the EMG signal from one or more other channels. For example, because the biceps and triceps work against each other, the NMES signals controlling the biceps and triceps, optionally depend on a linear combination of the EMG signal from the biceps and the EMG signal from the triceps, with a negative coefficient for the EMG signal from the triceps. If the linear combination is positive, only the biceps is stimulated, and if the linear combination is negative, only the triceps is stimulated. A similar method is optionally used for any other pair of agonist antagonist muscles, such as the flexors and extensors which also work against each other.

Optionally, the NMES signals are based not directly an the EMG signals from the corresponding muscles, but are modified to produce motion that is reversed in some way from the motion associated with the EMG signals. For example, if the EMG signals come from a left arm and the NMES signals are applied to a right arm, then optionally the NMES signals are changed to produce motion in the right arm that is the same as the motion of the left arm, rather than a mirror image of it, as would occur if the corresponding muscles in the two arms were to contract at the same time. Alternatively or additionally, whether or not the two arms are a left arm and a right arm, if the motion of the healthy arm is cyclical, then the NMES signals are changed to produce motion in the paretic arm that is 180 degrees out of phase from the motion of the healthy arm. Such a modification in the NMES signals might be particularly useful to use for the left and right legs, for example, in a patient who needs to relearn how to walk or ride a bike.

Optionally, there are also EMG electrodes 148, 150, 152, and 154, attached to the paretic arm. These sensors send signals along cables 156, 158, 160 and 162, respectively, to four additional channels of EMG device 120, which thus has a total of eight channels. These additional EMG signals are processed by the EMG device and by controller 124, similar to the processing of the EMG signals from healthy arm 102. Optionally, the EMG signals from paretic arm 146 are also used by controller 124 in controlling the NMES signals. The EMG signals in paretic arm 146 may arise because the sensory-motor cortex of the patient is still capable of producing weak nerve impulses in paretic arm 146, even if these nerve impulses are too weak to cause the paretic arm to move. By timing the NMES signals to the corresponding EMG signals in the paretic arm, the paretic arm can move in response to the attempts of the patient to move it, providing kinesthetic feedback to the patient. Alternatively or additionally, EMG signals in paretic arm 146 may be induced by moving paretic arm 146 passively, for example by a robot arm as discussed below in describing FIG. 3.

Figure 3:
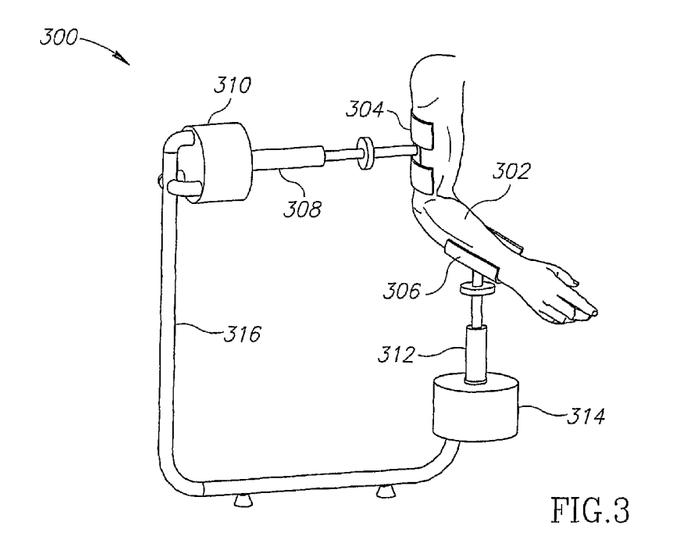
FIG. 3 is a schematic drawing of an arm attached to a robot arm, according to an exemplary embodiment of the invention.

Optionally, controller 124 also uses other information in controlling the strength of the NMES signals. For example, the healthy arm has a sensor 164, for example a strain sensor, which measures the degree of bending of the elbow, and a sensor 166 which measures the degree of extension of the fingers, while the paretic arm has similar sensors 168 and 170. The sensors feed into a unit 172 which processes the sensor data to determine the bending of the arm and fingers, and this information is conveyed, for example by cable 174, to controller 124. Optionally, unit 172 and controller 124 are part of a single control unit. Optionally, sensors are used only with one of the arms. Optionally there are other sensors which measure other aspects of the arm and hand position, particularly if EMG and NMES is used with additional muscles. A variety of other types of sensors are additionally or alternatively used for measuring the arm or hand position, for example the arm is fitted to a robot arm which has such sensors to measure its own state, as shown in FIG. 3 which will be described below. Or, LEDs are attached to key points on the arm and hand and their location tracked with a video camera, or magnetic field sensors are attached to key points on the arm and hand, and an external magnetic field and/or field gradient imposed. Other methods will be apparent to those skilled in the art of sensing the position and orientation of body parts.

The position of the paretic arm can be used, for example, as negative feedback to the NMES signals. During the course of rehabilitation, as the patient's own nerve impulses become stronger and/or more effective, for example distinguishing better between antagonistic pairs of muscles, the NMES signal can be reduced while producing the same arm motion. This kind of feedback can also be used within a given rehabilitation session. For example, if the patient is momentarily having trouble continuing to move his arm, the NMES amplitude is momentarily increased, until the patient is able to start moving his arm again. Optionally, in this case, the controller distinguishes between the patient simply resting, and the patient trying unsuccessfully to move his arm, for example by looking at EMG signal levels in the paretic arm.

The position of the healthy arm can be used, for example, to supplement the EMG signals from the healthy arm, as a measure of the degree of contraction of the muscles in the healthy arm. Alternatively or additionally, the data on position of both arms can be used to monitor the progress of the rehabilitation of the patient.

FIG. 3 shows an arm 302, which could be either the healthy arm or the paretic arm in FIG. 1, attached to a robot arm 300. The upper arm is held by a holder 304, and the lower arm is held by a holder 306. Upper arm holder 304 is attached to an extendable rod 308, which is connected to a controllable ball joint 310, and similarly lower arm holder 306 is attached to an extendable rod 312, which is connected to a controllable ball joint 314. Ball joints 310 and 314 are connected to each other with a rigid connector 316. The ball joints and extendable rods include both actuators and sensors, for all their degrees of freedom, in this case two degrees of freedom for each ball joint, and one degree of freedom for each extendable rod. The sensors can sense the degree of bending of the elbow of arm 302, and the actuators can apply force to bend or unbend the elbow, and/or to resist bending or unbending of the elbow by the patient. Optionally, the actuators and sensors have more or fewer degrees of freedom, depending for example on which muscles are being rehabilitated, and optionally the robot arm is attached to additional points on arm 302, for example to different points on the wrist, hand, and fingers. Signals from the sensors and to the actuators are processed by a robot arm control box, not shown in FIG. 3.

The robot arm optionally is used in the same way as sensors 164, 166, 168 and 170 in FIG. 1. In addition, the fact that the robot arm can move in a controlled way under its own power means that it can supplement the AMES, in providing kinesthetic feedback for the patient, if used with the paretic arm. The robot arm provides a different kind of kinesthetic feedback than NMES provides, since it moves the paretic arm without causing muscles to contract under their own power, and both types of feedback are potentially useful in rehabilitation. For example, NMES may not be able to produce a smooth and accurate motion by itself, and robot arm can help to correct and smooth the motion induced by NMES.

Optionally, both the passive and active modes of the robot arm are combined with the NMES. Movement generated by the robot arm is assisted by contraction of the muscles by NMES. When the patient moves the robot arm an active way, the NMES signals are adjusted correspondingly.

Optionally, motion of the robot arm attached to the paretic arm is based on EMG readings in combination with motion of the healthy arm.

When providing rehabilitation various types of motion may be supported by the robotic arm, for example, one or more of:

a) Passive motion. The robot arm is moved and the patient moves with it.

b) Resisted motion. The patient moves the robot arm and encounters resistance. The resistance may be of various magnitudes and may be uniform in all direction or be directional.

c) Assisted motion. When a patient moves the robot arm, a positive feedback on arm increases the force of motion in the direction moved by the patient.

d) Force field motion. The patient moves the robot arm. Along a certain trajectory one level of resistance (or none) is encountered Deviation from the trajectory is not allowed or meets with resistance. Motion along a "correct" trajectory can be without resistance, or possibly assisted. An increased resistance is exhibited in a volume surrounding trajectory. An even greater resistance is exhibited in a surrounding volume. A prevention of motion may be provided in an outside volume. In an exemplary embodiment of the invention, a corrective force vector is applied when not on trajectory, pointing towards trajectory. Optionally, instead of a corrective force, resistance varies as a function of distance from trajectory, thus, motion of the robot arm is naturally urged back to trajectory. Optionally, the force is applied in the direction of the path. Alternatively, the force maybe a unidirectional force of resistance.

This type of motion helps to train the patient in a desired motion.

e) Mirrored motion. Motion of the robot arm is required to mirror the trajectory of motion of a different element, for example for dual limb rehabilitation.

f) Free motion. Patient moves the robot arm in any way he desires, possibly receiving feedback. As the patient (or therapist or helper) moves the robot arm, a device may record it for future playback. In a playback mode the prerecorded motion (or path) is optionally reconstructed using other modes. Optionally, the recorded path is modified (e.g., smoothed), for example automatically or manually.

g) General Force Field. A force field and/or an assistance field is defined which is not related to any particular trajectory. For example, a range of trajectories may be allowed to be practiced by a user, or a real or virtual situate on simulated (e.g., water, areas with obstacles).

h) Local force field. A force field which is applied to only a small locality and/or only in one or two dimensions.

i) Restricted motion. One or more points of the body of a subject are supported or prevented from moving. Optionally, the angles between such points and the moving points on the device are measured. In one example the elbow is locked with a dedicated harness allowing only a shoulder motion. In some embodiments, the restriction is partial and/or is provided by a movable element (e.g., an arm).

j) Initiated Motion. The patient initiates the motion (e.g., a 1 cm motion or 100 gram force) and the robot arm completes or helps the patient complete the motion in space. The completion may be of a whole trajectory or of part of a trajectory.

k) Implied motion. The robot arm begins the motion and the patient completes it. The robot arm may assist the rest of the motion in various manners (e.g., by changing to one of the modes described herein after the motion starts). If the patient fails to pick up the motion, the robot arm may generate a cue, for example an audio reminder. Different parts of a single motion trajectory may each have a machine initiation definition. Optionally, if a patient is too slow in moving, the robot arm begins the motion.

l) Cued motion. The patient receives a cue from the system before motion according to a different mode begins. The cue can be, for example, vibration of the robot arm, stimulation pads on the skin, audio or visual cue. In some embodiments of the invention, the strength of the cue and/or its timing and/or other ongoing activities (e.g., a visual display and game) are used to help train the coordination between different modalities, for example, hand-eye coordination. A motion cue can be used to train a kinesthetic sense.

m) Teach Mode. The robot arm is taught a motion. In one example, a therapist performs a motion and motion parameters at each point are recorded and can then be used for an exercise. Another way of teaching the system is to follow a path that the therapist traces with his/her own motion. The therapist may use the controller to indicate a point to be taught or a continuous mode may be defined by which an entire trajectory is learned. Optionally the path and points are edited before replay. Optionally, the paths are processed, for example, by smoothing or identifying motion points, before playback.

Thus, in some embodiments of the invention, the robot arm can provide one or more of Isokinetic, Isotonic and Isostatic exercises.

It should be appreciated that a definition of a trajectory which the robot arm is to follow can include speed parameters. For example, a user may be assisted, or urged, or expected, to move the robot arm at a certain speed. The speed may be, for example, absolute, or relative (e.g., requiring a uniform speed or the speed to match a non-uniform profile).

Optionally, an angular trajectory is defined, which places constraints on an angular orientation of the robot arm. In some embodiments, the constraint is one dimensional. In others it is two or three dimensional.

Speed, angles and spatial trajectories in a particular rehabilitation scenario may each belong to a different one of the above motion types. For example, spatial trajectory may be of a force field type, while speed trajectory is free or assisted. The type of trajectory and/or its parameters may also vary along the trajectory, as a function of time and/or as a function of previous performance. For example, a smaller assistance at a later part of a trajectory may be provided for a type of motion which was properly (or better than expected) executed in an earlier part of the trajectory.

Trajectories may be absolute, for example, defined as a function of a resting point or a different point on the robot arm. In other embodiments, the trajectories are purely relative, for example, requiring a patient to move an arm in a straight line, regardless of starting point. In other embodiments, a trajectory is partially relative, in that once motion starts, this determines the shape of the rest of the trajectory, for example, a start of a trajectory indicating if a patient is standing or sitting, and thus what type of hand motion is expected.

In some embodiments, such as described below, where multiple points are defined, the trajectories of each point may be of different types. In some embodiments, what is defined is a trajectory as a function of two or more points. For example, if two points are used to define an elbow configuration (e.g., angle between bones), the trajectory constraints may be defined on the motion of the elbow. Such motion may be relative in space (e.g., a comparison of the two points) and not absolute (e.g., compared to a device reference point). It should be noted that in some embodiments of the invention a tensor or tensor field is provided, as each point in space can have associated with it a speed, a force and/or a rotation, all of which can be scalar or a vector.

In some embodiments of the invention, different modes are defined for different parts of a trajectory or for different parts of space (e.g., for a particular arm). Optionally, a mode may be triggered based on the actual performance. For example, if motion velocity is below a certain threshold, a more assistive mode is provided. Similarly, a pause of over a threshold may imply a more assistive mode. An exact motion may imply a less assistive mode.

Figure 4:
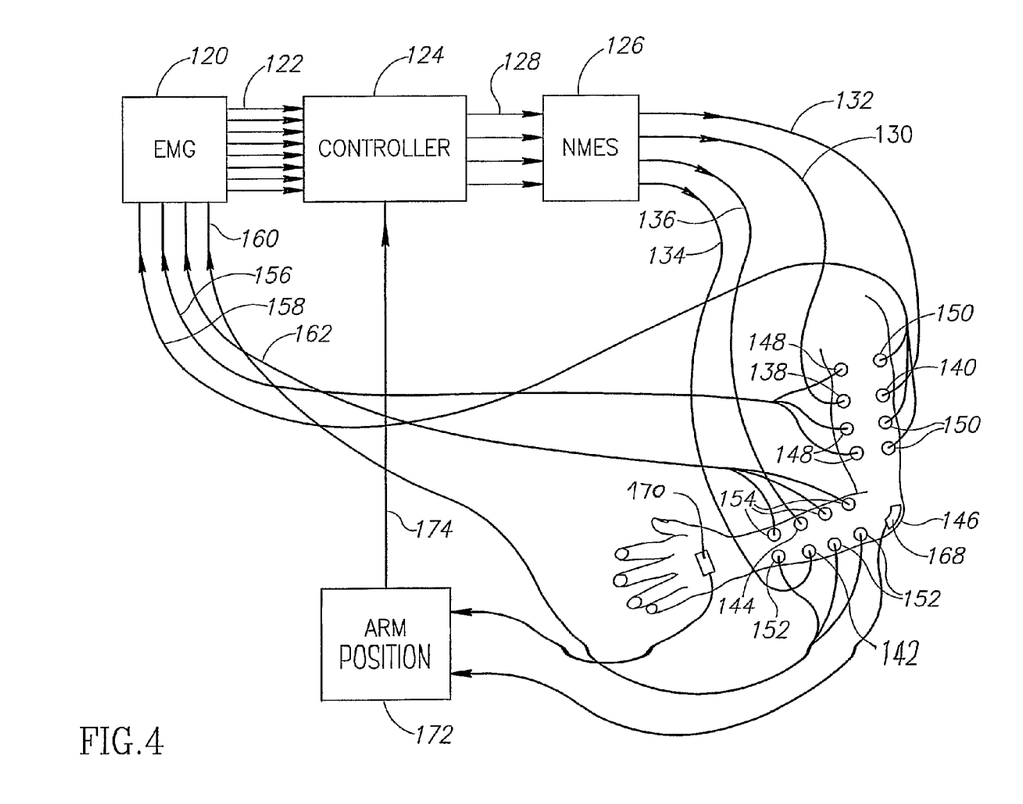
FIG. 4 is a schematic drawing of a paretic arm with NMES electrodes and EMG electrodes, nerve signals from brain, and a signal processing unit, according to a different exemplary embodiment of the invention than FIG. 1.

FIG. 4 shows an arrangement according to another exemplary embodiment of the invention, in which only a paretic arm 146 is used. As in FIG. 1, there are EMG electrodes 148, 150, 152 and 154, attached respectively to the biceps, triceps, flexors and extensors of the paretic arm, three electrodes for each muscle, and the EMG signals are conveyed along cables 156, 158, 160, and 162, to an EMG device 120, which, after preliminary processing, transmits the signals to controller 124. As in FIG. 1, controller 124 uses the EMG signals in determining the amplitude and timing of NMES signals transmitted by NMES device 126, which stimulate the biceps, triceps, flexors and extensors of paretic arm 146 through NMES electrodes 138, 140, 142, and 144.

The NMES signals transmitted by NMES device 126 in FIG. 4 are not strong enough, in themselves, to cause paretic arm 146 to move significantly, and this is optionally also true in FIG. 1. But the NMES signals, together with the patient's own nerve impulses, are strong enough to cause the arm to move. Thus, the paretic arm only moves when the patient tries to move it, and the kinesthetic feedback provided by the motion further encourages the development of alternate pathways for nerve impulses in the patient, or alternate locations in the motor cortex to originate nerve impulses to the same muscles, eventually enabling the patient to move the paretic arm by himself. This may be particularly useful when the motion involves a coordinated sequence of contractions of more than one muscle. Optionally, in the course of rehabilitation, the NMES signal is lowered, as less NMES signal is needed in order to allow the patient to move the paretic arm.

Optionally, in the absence of nerve impulses from the patient's motor cortex, the NMES signals are between 100% and 120% of the amplitude needed to produce motion for an average healthy subject, or for an average paretic patient, or they are adjusted to that level for a particular patient. Alternatively, they are between 120% and 140% of that amplitude for any of these people, or between 80% and 100%, or between 60% and 80%, or less than 60%. Optionally, for any of these people, the NMES signals are between 100% and 120% of the level needed to produce motion in the presence of nerve impulses from the motor cortex when the person makes an effort to move, or between 120% and 140%, or between 140% and 200%, or greater than 200%.

Optionally, the NMES is targeted to a part of the muscle with at least as much spatial precision as an average healthy subject is able to achieve when voluntarily directing nerve impulses to that muscle. Alternatively, the NMES is targeted with less than this much precision, but with at least half this much precision, or with less than half this much precision, but at least one quarter this much precision, or with less than one quarter this much precision.

Characteristics of the procedure illustrated in FIGS. 1 and 4 can be varied to adapt to the needs of the patient, in order to facilitate rehabilitation. Several examples are given below.

The EMG and NMES need not use the four muscles shown being used in FIGS. 1 and 4, but could include more muscles, or fewer muscles. Optionally, only the biceps and triceps are used initially. Then, once the patient has gained some ability to use the biceps and triceps effectively, the flexors and extensors are added to the EMG and NMES channels. These four muscles are basic to gross control of the arm, in addition to other muscles such as the pectorals and the deltoids. Later, individual fingers are added, and/or other wrist and hand motions, to improve fine motor control. For rehabilitation of body parts other than the arm, of course, other groups of muscles are selected.

The amplitude of NMES optionally varies depending on feedback from various sources, and depending on the immediate goal of the rehabilitation program. As mentioned previously, the NMES signal is optionally decreased as the patient recovers the ability to generate nerve impulses and move his muscles by himself. Alternatively, if the immediate goal is the strengthening of atrophied muscles, the amplitude of NMES is optionally increased as the muscle gets stronger, and can benefit from more strenuous exercise. In this case, the arm is optionally made to move against a restraining force, for example a weight or a robotic arm, which is increased as the muscle gets stronger, so a stronger NMES signal is required in order to move the arm by the same amount.

In addition to using kinesthetic feedback to encourage the development of alternative pathways for nerve impulses, as discussed above, other kinds of feedback are optionally used to help the patient learn how to control his muscles more effectively. For example, seeing the movement of the arm, when his nerve impulses are supplemented by NMES stimulation, can help the patient adjust his efforts to move his arm. Similarly, such feedback for conscious learning by the patient can be provided by a device, such as the robot arm in FIG. 3, which measures and records the motion of the arm, and by the processed EMG signals. For example, the patient can try to make the EMG signals from the paretic arm more closely resemble the EMG signals generated by the healthy arm when it is performing the desired movement, or he can try to make the EMG signals from the paretic arm more closely resemble some template, perhaps developed from examining recorded EMG signals from the healthy arm, or from paretic arms of other patients who have undergone similar rehabilitation.

In the arrangement shown in FIG. 1, if the patient's other arm is used as the healthy arm, then optionally the patient tries to move both arms synchronously, in mirror image movements. The NMES signals, optionally based on the EMG signals of the healthy arm, allow the paretic arm to move, and since the patient is attempting to move both arms in synchrony, he receives kinesthetic feedback from the paretic arm, which helps promote the development of alternate pathways for nerve impulses. In some embodiments of the present invention, movement of the paretic arm to mirror movement of the healthy arm is assisted, in part or in whole, by the robotic arm 300.

Optionally, the NMES signals are adapted to the capability of the paretic arm. For example, if the muscles in the paretic arm are incapable of responding as rapidly as normal to the NMES, then the NMES signals are optionally slowed down, or high frequency components are reduced or removed. As the muscles recover the capability of more rapid response, the NMES signals are sped up again. The speed of the NMES signals is either adjusted automatically, in response to sensor data on movement of the paretic arm, or manually by the therapist, optionally using such sensor data to evaluate the patient. If a robotic arm is used in coordination with NMES to help move the paretic arm, the motion of the robotic arm is optionally slowed down together with the NMES. Even if the robotic arm is used to help move the paretic arm without NMES, the motion of the robotic arm is optionally slowed down if, for example, this will help the patient to make a greater contribution to the motion with his own nerve impulses, or will be useful for some other reason in rehabilitation.

Figure 5A:
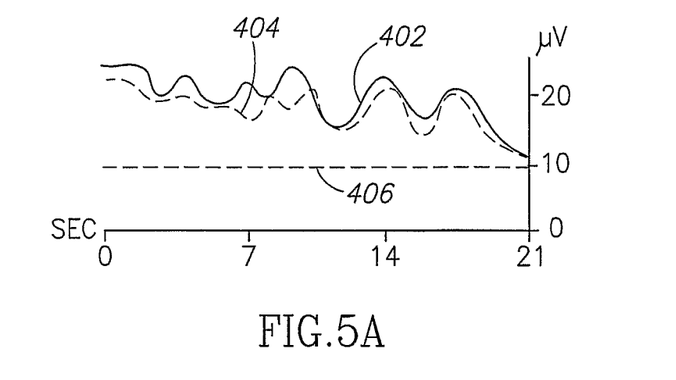
FIGS. 5A-5G are a time sequence of plots of EMG signals from flexor and extensor signals, at different times during rehabilitation, according to an exemplary embodiment of the invention.
Figure 5B:
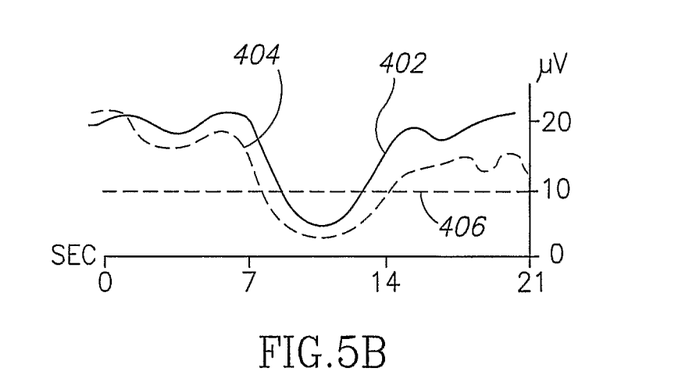
Figure 5C:
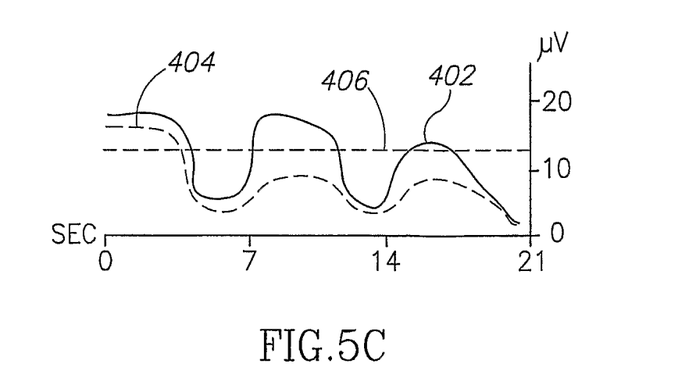
Figure 5D:
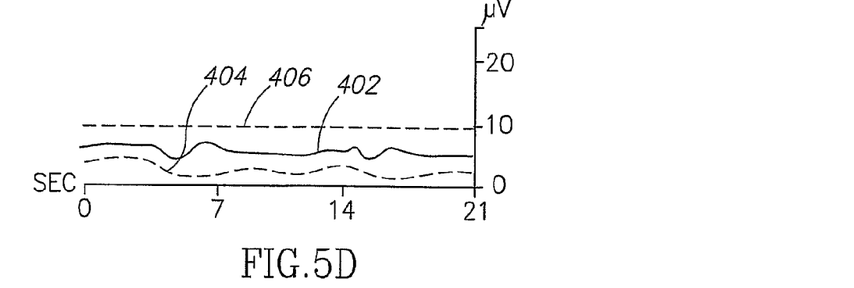
Figure 5E:
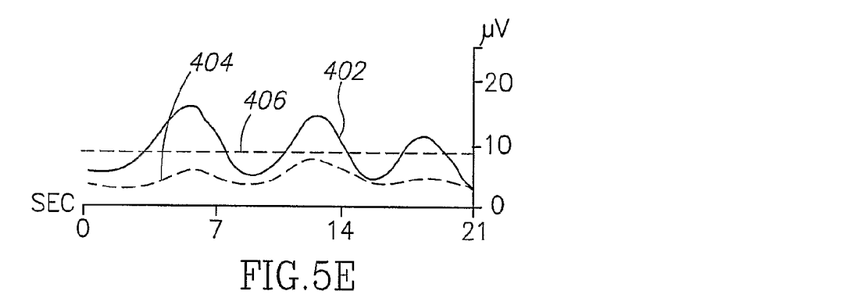
Figure 5F:
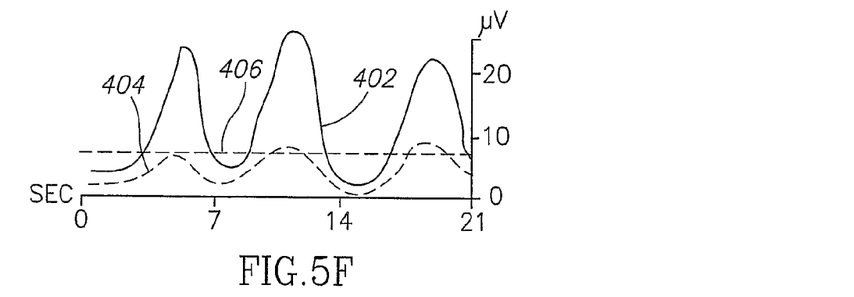
Figure 5G:
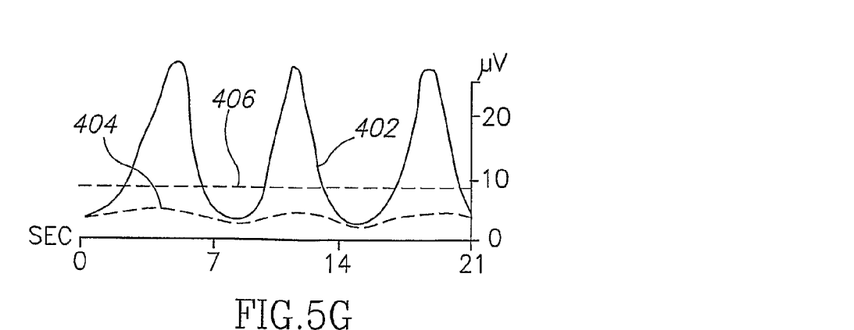

FIGS. 5A through 5G illustrate a procedure for rehabilitating a patient who has a problem that is common following a stroke in the somato-motor cortex—the failure of the patient's nerve impulses to distinguish adequately between two muscles that form an antagonistic pair, such as the biceps and triceps, or the flexors and extensors. As shown in FIG. 5A, the EMG signal 402 from the flexors, and signal 404 from the extensors, when the patient attempts to open and close her hand, are strong enough to cause both muscles to contract, since they are above threshold level 406. But both muscles contract at the same time, so that they work against each other, and the hand exhibits very little movement. First, the patient learns to decrease the overall activity of both the flexors and extensors, below the threshold for contraction, as shown progressively in FIGS. 5B, 5C, and 5D. Then, as shown in FIGS. 5E, 5F, and 5G, the patient is taught to increase the activity of the extensors, while keeping the flexors relaxed. This is done, for example, by, applying NMES to the extensors, increasing kinesthetic feedback, when patient tries to contract the extensors.

To summarize, listed below are some of the rehabilitation methods that can be used in some embodiments of the invention, including those discussed.

1) Record EMG in healthy arm and apply similar pattern of NMES to paretic arm, in real time or not.
2) Adjust NMES amplitude to supplement nerve impulses in paretic arm, as measured by EMG in paretic arm.
3) Target NMES to sections of paretic arm where EMG is weak.
4) Slow down NMES to adapt to slow response time of paretic arm.
5) Have patient move both arms together, in mirror image, while applying NMES based on EMG in healthy arm.
6) Have patient move both arms together not in a mirror image, and/or in a cyclical motion 180 degrees out of phase, while applying NMES based on (but modified from) EMG in healthy arm.
7) Base NMES on average EMG over many repetitions of movement by healthy arm.
8) Sense position of paretic arm and use negative feedback for NMES; optionally use EMG of paretic arm to distinguish inability to move arm from intentional resting.
9) Record sensed position of healthy arm as a function of time while recording EMG signals, then apply corresponding NMES to paretic arm when paretic arm is in a corresponding position.
10) Use robotic arm to move healthy arm in a desired pattern, detect the resulting EMG signals generated passively in the healthy arm, and use them as a basis for NMES applied to paretic arm to produce corresponding motion.
11) Use robotic arm and/or NMES to move or assist moving paretic arm, matching to measured position of healthy arm.
12) Use robot arm to measure resistance of paretic arm to motion, thereby determining whether failure of paretic arm to move is due to failure of muscle to contract, or failure to differentiate between antagonistic pairs of muscles; optionally adjust NMES accordingly.
13) Use robotic arm, with or without NMES, to assist moving paretic arm, slowing down robotic arm to match capability of paretic arm.
14) Use robotic arm to work against muscles of paretic arm, with or without NMES, optionally adapting force to capability of paretic arm.
15) Use EMG of paretic arm to teach patient to better control paretic arm, optionally including better differentiating between antagonistic pairs of muscles.

In an exemplary embodiment of the invention, the method of applying NMES is combined with the teachings of other applications filed by the applicant.

U.S. provisional application No. 60/633,442 filed on Dec. 7, 2004, also being filed as PCT application on same date as the present application and by the same applicant, entitled "Methods and Apparatuses for Rehabilitation Exercise and Training", the disclosures of which are incorporated herein by reference, describe rehabilitation of balance. In an exemplary embodiment of the invention, NMES is used to help a patient coordinate two sides of a body, or to stimulate muscle sin one part of the body relating to balance (e.g., a torso) when another part moves (e.g., legs).

U.S. provisional application No. 60/566,079 filed on Apr. 29, 2004, also being filed as PCT application on same date as the present application and by the same applicant, entitled "Fine Motor Control Rehabilitation", the disclosures of which are incorporated herein by reference, describe rehabilitation of fine motor control. In an exemplary embodiment of the invention, NMES is used to help a patient coordinate gross and fine motor motions (e.g., measuring a large muscle and stimulating a small muscle or vice versa) or to copy fine motor control from a healthy arm to a paretic arm.

U.S. provisional application No. 60/633,428 filed on Dec. 7, 2004, also being filed as PCT application on same date as the present application and by the same applicant, entitled "Gait Rehabilitation Methods and Apparatuses", the disclosures of which are incorporated herein by reference, describe rehabilitation of gait. In an exemplary embodiment of the invention, NMES is used to coordinate the movement of two legs and/or of motion of different parts of a leg, for example, EMG measurements on a thigh (healthy or paretic) are used to drive NMES signals to a paretic calf.

U.S. provisional application No. 60/542,022 filed on Feb. 5, 2004, also being filed as PCT applications on same date as the present application and by the same applicant, entitled "Methods and Apparatus for Rehabilitation and Training", the disclosures of which are incorporated herein by reference, describe rehabilitation devices of various types. In an exemplary embodiment of the invention, NMES stimulation and/or EMG measurement is provided in such devices.

U.S. provisional application No. 60/604,615 filed on Aug. 25, 2004, the disclosure of which is incorporated herein by reference, describes rehabilitation while measuring and/or otherwise taking into account brain plasticity. In an exemplary embodiment of the invention, NMES stimulation is provided in a manner which is coordinated with the activity of brain centers responsible for generating neural signal to the paretic limb and/or to receive signals form the paretic limb. Such a brain area may be detected, for example using EEG or fMRI methods.

As used herein, a "position" of an arm or another body part may include not just the spatial location of a particular portion of the arm or body part, but any other information needed to specify its spatial state, including, for example, how much it is bent at the elbow, how much the forearm is twisted, how much the wrist is bent, etc. In some embodiments, the velocity of the part and/or its orientation are controlled.

The invention has been described in the context of the best mode for carrying it out. It should be understood that not all features shown in the drawing or described in the associated text may be present in an actual device, in accordance with some embodiments of the invention. Furthermore, variations on the method and apparatus shown are included within the scope of the invention, which is limited only by the claims. Also, features of one embodiment may be provided in conjunction with features of a different embodiment of the invention. As used herein, the terms "have", "include" and "comprise" or their conjugates mean "including but not limited to."

The invention claimed is:

1. Apparatus for rehabilitating a patient who has a paretic body part, the apparatus comprising:
   a) at least one electromyography (EMG) sensor adapted to be applied to a voluntary muscle of a healthy body part of the same type as the paretic body part, wherein at least one sensor produces at least one EMG signal;
   b) a neuromuscular electrical stimulation (NMES) device adapted for stimulating at least one voluntary muscle of the paretic body part; and,
   c) a controller which controls the NMES device, the controller being configured to
      (i) store a desired motion of the paretic body part,
      (ii) store NMES amplitude insufficient to cause the desired motion,
      (iii) determine an amplitude of stimulation of the paretic body part at least partly based on the EMG signal from the healthy body part and the stored desired motion of the paretic body part such that the NMES stimulation is not sufficient, on its own, to move the paretic body part in the desired motion, and,
      (iv) apply stimulation to the paretic body part using the NMES device while detecting at least one EMG signal from the healthy body part.

2. Apparatus according to claim 1, wherein the at least one muscle of the healthy body part corresponds to the at least one muscle of the paretic body part.

3. Apparatus according to claim 1, wherein the controller is configured to process the at least one EMG signal and determine at least one property of the NMES signal.

4. Apparatus according to claim 2, wherein the controller is configured so that the NMES device stimulates the paretic body part to make a movement corresponding to a movement in a pattern of movement made by the healthy body part when the EMG signals are sensed.

5. Apparatus according to claim 4, wherein the controller is configured so that the amplitude of stimulation of at least one of the at least one muscle of the paretic body part increases when the EMG signal from the corresponding muscle of the healthy body part increases at a corresponding time interval in the pattern of movement of the healthy body part.

6. Apparatus according to claim 4 or claim 5, wherein the at least one muscle of the paretic body part comprises an antagonistic pair of muscles, and the controller is configured so that the amplitude of stimulation of one muscle of the antagonistic pair of muscles decreases when the EMG signal from the muscle in the healthy body part corresponding to the other muscle of the antagonistic pair of muscles increases at a corresponding time interval in the pattern of movement of the healthy body part.

7. Apparatus according claim 1, wherein one or both of the controller and the NMES device are configured to store a stimulation amplitude that is not high enough to cause the stimulated muscle to contract in the absence of nerve impulses from the patient's brain, but is high enough to cause the muscle to contract in the presence of nerve impulses from the patient's brain, for at least some patients who cannot move the body part by themselves.

8. Apparatus according to claim 1, wherein the at least one EMG sensor comprises a plurality of EMG sensors, each EMG sensor adapted to be applied to a different muscle or muscle part of the healthy body part.

9. Apparatus according to claim 8, wherein each EMG sensor produces a separate EMG signal.

10. Apparatus according to claim 9, wherein the NMES device is adapted to independently stimulate a plurality of muscles or muscle parts of the paretic body part.

11. Apparatus according to claim 10, wherein the plurality of muscles or muscle parts of the paretic body part correspond to the muscles or muscle parts of the healthy body part to which the plurality of EMG sensors are adapted to be applied.

12. Apparatus according to claim 11, wherein the controller is configured so that amplitude of NMES stimulation of the plurality of muscles or muscle parts of the paretic body part is at least partly dependent on the EMG signals from the plurality of EMG sensors.

13. Apparatus according to claim 12, wherein the controller is configured so that the amplitude of NMES stimulation of each of the plurality of muscles or muscle parts depends at least partly on the EMG signal from the corresponding muscle or muscle part.

14. Apparatus according to claim 1, wherein the paretic body part is a body part that comes in pairs.

15. Apparatus according to claim 14, wherein the paretic body part is an arm.

16. Apparatus according to claim 14, wherein the paretic body part is a leg.

17. Apparatus according to any of claims 14-16, wherein the healthy body part belongs to the patient.

18. Apparatus according to any of claims 14-16, wherein the healthy body part belongs to a different person.

19. Apparatus according to claim 1, wherein the controller makes the stimulation amplitude at least partly dependent on a processed form of the EMG signal.

20. Apparatus according to claim 19, wherein the processed form of the EMG signal is stretched out in time from the EMG signal.

21. Apparatus according to claim 19 or claim 20, wherein the processed form of the EMG signal corresponds to an EMG signal that would be produced by a movement of the healthy body part that is a mirror image of a movement that the healthy part was undergoing when the EMG signal was generated.

22. Apparatus according to claim 19, wherein the processed form of the EMG signal is time delayed from the EMG signal.

23. Apparatus according to claim 1, also including a first position sensing device which monitors a position of the healthy body part.

24. Apparatus according to claim 1, also including a second position sensing device which monitors a position of the paretic body part.

25. A method of rehabilitating a patient who has a paretic body part, the method comprising:
   a) having the patient or another person move in a movement pattern a healthy body part that is of the same type as the paretic body part;
   b) detecting electromyography (EMG) signals from the healthy body part while it is being moved;

c) processing the EMG signals to determine at least one property of a neuromuscular electrical stimulation (NMES) signal;
d) applying the NMES signal to the paretic body part, responsive to the processing; and
e) moving the paretic body part partially by the NEMS stimulation.

26. A method according to claim 25, wherein the NMES signal is applied at a timing in the movement pattern according to the EMG signals.

27. A method according to claim 25, wherein the NMES signal is applied at an amplitude according to the EMG signals.

28. A method according to claim 25, also including having the patient attempt to move the paretic body part, while the NMES signal is applied, in the same movement pattern that the healthy body part is moved in while the EMG signals are detected.

29. A method according to claim 28, wherein detecting the EMG signals comprises detecting the EMG signals from a plurality of muscles or muscle parts of the healthy body part, and applying NMES comprises applying NMES to a plurality of muscles or muscle parts of the paretic body part corresponding to the plurality of muscles or muscle parts of the healthy body part.

30. A method according to claim 29, wherein the amplitude of NMES applied to each muscle or muscle part of the paretic body part during a time interval in a pattern of attempted movement of the paretic body part depends at least partly on the EMG signal detected from the corresponding muscle or muscle part of the healthy body, during a corresponding time interval in the movement pattern of the healthy body part.

31. Apparatus according to claim 1, wherein the paretic body part is an arm.

32. A method according to claim 25, wherein the paretic body part is an arm.

* * * * *